(12) United States Patent
Park et al.

(10) Patent No.: US 9,342,482 B2
(45) Date of Patent: May 17, 2016

(54) ON-CHIP SPECTRAL ANALYSIS USING ENHANCED RECURSIVE DISCRETE FOURIER TRANSFORMS

(71) Applicant: Texas Instruments, Incorporated., Dallas, TX (US)

(72) Inventors: Joonsung Park, Dallas, TX (US); Srinadh Madhavapeddi, Dallas, TX (US); Christopher Barr, Plano, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 797 days.

(21) Appl. No.: 13/674,941

(22) Filed: Nov. 12, 2012

(65) Prior Publication Data

US 2014/0136138 A1  May 15, 2014

(51) Int. Cl.
| | | |
|---|---|---|
| *G01R 23/00* | (2006.01) | |
| *G06F 17/00* | (2006.01) | |
| *G01R 23/16* | (2006.01) | |
| *G01R 31/28* | (2006.01) | |
| *G01R 31/317* | (2006.01) | |
| *G06F 11/22* | (2006.01) | |
| *G06F 11/24* | (2006.01) | |
| *G01N 29/46* | (2006.01) | |
| *G06F 17/14* | (2006.01) | |

(52) U.S. Cl.
CPC ............... *G06F 17/00* (2013.01); *G01R 23/16* (2013.01); *G01R 31/28* (2013.01); *G01R 31/3172* (2013.01); *G06F 11/2294* (2013.01); *G06F 11/24* (2013.01); *G01N 29/46* (2013.01); *G01R 31/31721* (2013.01); *G01R 31/31727* (2013.01); *G06F 17/141* (2013.01)

(58) Field of Classification Search
USPC .......................................................... 702/112
See application file for complete search history.

(56) References Cited

U.S. PATENT DOCUMENTS

| | | | |
|---|---|---|---|
| 5,420,516 A * | 5/1995 | Cabot ............................ 324/620 |
| 2003/0040875 A1* | 2/2003 | Rao et al. ........................ 702/76 |
| 2003/0040876 A1* | 2/2003 | Rao ................................. 702/76 |
| 2005/0002473 A1* | 1/2005 | Kloper et al. ................. 375/316 |
| 2006/0047450 A1* | 3/2006 | Tabatabaei et al. ............. 702/69 |
| 2010/0058867 A1* | 3/2010 | Ueno et al. ...................... 73/587 |
| 2012/0041994 A1* | 2/2012 | Smith et al. ................... 708/207 |
| 2013/0046805 A1* | 2/2013 | Smith et al. ................... 708/404 |
| 2013/0165734 A1* | 6/2013 | Butters .......................... 600/13 |
| 2013/0173680 A1* | 7/2013 | Lei et al. ....................... 708/405 |

* cited by examiner

*Primary Examiner* — Paul D Lee
(74) *Attorney, Agent, or Firm* — John R. Pessetto; Frank D. Cimino

(57) ABSTRACT

A computing device uses a recursive discrete Fourier transform (RDFT) engine to reduce time required by a frequency transform module, memory required to hold intermediate products, and/or computing resources used for the testing. In an embodiment the windowing function is integrated and processed simultaneously with the recursive DFT funcions. A frequency-bin power module is configured to determine the frequency bin within the set of frequency bins that has a greatest signal power at various levels of recursion.

20 Claims, 4 Drawing Sheets

ON-CHIP SPECTRAL ANALYSIS USING ENHANCED RECURSIVE DISCRETE FOURIER TRANSFORMS

BACKGROUND

The proper operation of electronic devices can be determined by analyzing the spectral characteristics of the devices. For a variety of mixed-signal designs, many of the important specifications are measured by transforming time-domain information to the spectral-domain. Conventionally, spectral-domain analyses are typically performed off-chip using an FFT (fast Fourier transform) and/or DFT (discrete Fourier transform) algorithm, which requires ever-increasingly large number of samples to obtain greater frequency resolution, for example. Performing such measurements on-chip using built-in self-testing (BIST) techniques often involves increased power consumption and data rates, larger circuit layouts, increased pin counts, increased manufacturing costs, and the like.

SUMMARY

In general, one implementation of the subject matter disclosed herein is directed to determining spectral characteristics of a circuit, which is disposed on a substrate, using a digital or signal processor, which is also disposed on the substrate. The processor includes a frequency transform module that is configured to perform a first-level transform of a first size on the windowed test data to yield a set of frequency bins, wherein each frequency bin in the set of frequency bins includes an indication of a signal power of the respective frequency bin. The processor includes a frequency-bin power module that is configured to determine a frequency bin within the set of frequency bins that has a greatest signal power.

The Fourier transform module is further configured to perform a second-level frequency transform of a second size on the frequency bin within the set of frequency bins that has the greatest signal power to yield a subordinate group of frequency bins. Each frequency bin in the subordinate group of frequency bins includes a signal power. The frequency-bin power module is further configured to determine a subordinate group frequency bin within the subordinate group of frequency bins that has a greatest signal power. The processor includes a spectral-characteristics module that is configured to use the subordinate group frequency bin that has the greatest signal power to determine the spectral characteristics of the test data.

This Summary is submitted with the understanding that it is not be used to interpret or limit the scope or meaning of the claims. Further, the Summary is not intended to identify key features or essential features of the claimed subject matter, nor is it intended to be used as an aid in determining the scope of the claimed subject matter.

DETAILED DESCRIPTION

Figure 1:
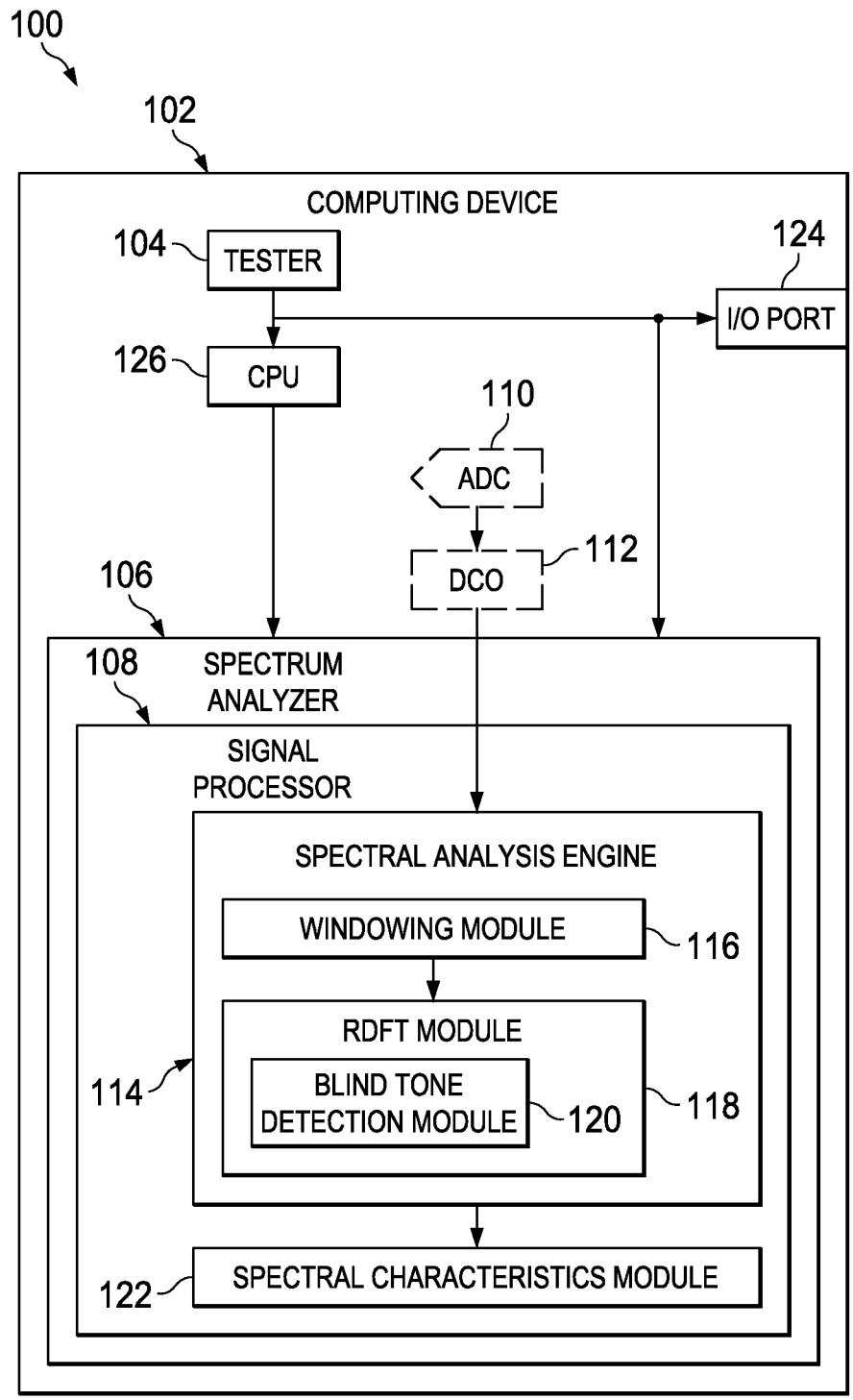
FIG. 1 shows an illustrative computing device in accordance with exemplary embodiments of the disclosure.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description—and claims—to refer to particular system components. As one skilled in the art will appreciate, various names may be used to refer to a component. Accordingly, distinctions are not necessarily made herein between components that differ in name but not function. In the following discussion and in the claims, the terms "including" and "comprising" are used in an open-ended fashion, and thus are to be interpreted to mean "including, but not limited to . . . ." Also, the terms "coupled to" or "couples with" (and the like) are intended to describe either an indirect or direct electrical connection. Thus, if a first device couples to a second device, that connection can be made through a direct electrical connection, or through an indirect electrical connection via other devices and connections.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

A computing device is disclosed herein that is disposed on a substrate and which is tested using a processor that is also disposed on the same substrate. Testing of the computing device is performed to calculate spectral characteristics of the computing device. The spectral characteristics are used (for example) to determine the specification parameters for the computing device. The test results are used for calibrations purposes to improve the performance of the computing device. For many such computing devices, input/output (I/O) pins (pads, terminals, ports, and the like) are precious assets. As a result, testing the computing device on-chip conserves I/O pins that would otherwise be used to transmit test results off the chip. Additionally, testing the computing device on-chip allows calculations that use at-speed parallel outputs to likewise be performed on-chip. One or more implementations read out the calculations serially at lower speeds.

FIG. 1 shows an illustrative computing device in accordance with exemplary embodiments of the disclosure. For example, a computing device 102 arranged on a substrate 100 includes a tester 104, a spectrum analyzer 106, a signal processor 108, an analog-to-digital converter (ADC) 110, a digitally controlled oscillator (DCO) 112, and a spectral analysis engine 114.

The illustrated spectral analysis engine 114 includes a windowing module 116 and a recursive discrete Fourier transform (RDFT) module 118. The illustrated RDFT module 118 includes a blind tone detection module 120.

The illustrated spectrum analyzer 106 includes a spectral characteristics module 122. The illustrated computing device 102 also includes an input/output (I/O) port 124 and a central processing unit (CPU) 126.

In one or more implementations, the computing device 102 is incorporated into a personal computing device, such as a cell phone, a laptop computer, digital versatile disk (DVD) player, a desktop computer, a tablet computer, or the like. The computing device 102 typically includes one or more embedded analog mixed-signal (AMS) "intellectual property" (IP) cores arranged as a systems-on-chip (SoCs), where the SoC is arranged on a common substrate such as substrate 100.

In one or more implementations, the tester 104 generates test vectors on-chip to be applied to the spectrum analyzer 106. For example, the tester 104 can generate test patterns, which is a computerized test pattern generator based on an underlying algorithm. The test patterns include frequency information of having known parameters such that measured test results can be compared against the known parameters. The tester 104 can include an analog signal generator, digital waveform synthesizer, or other suitable test signal generator.

In one or more implementations, the spectrum analyzer 106 is any suitable circuitry that is capable of analyzing the spectral components of electrical signals. Such spectral components include frequency, total harmonic distortion, signal-to-noise ratio (SNR), power, bandwidth, and the like.

In one or more implementations, the signal processor 108 is any suitable processor that includes either digital circuits or a combination of analog and digital circuits on the same semiconductor die. For example, the signal processor 108 may include analog-to-digital converters such as the ADC 110. The signal processor 108 may include digitally controlled circuits such as the digitally-controlled oscillator (DCO) 112 and digitally-controlled audio/RF (radio frequency) circuits. The signal processor 108 also may include digital-to-analog converters (DAC). The signal processor 108 may be part of a system-on-chip (SoC) of the computing device 102. In an embodiment, the methods and systems disclosed herein are performed using digital signal processing and thus can be implemented using hardware, software, or any suitable combination of hardware and software In one or more implementations, the analog-to-digital converter (ADC) 110 is any suitable circuitry that is capable of converting an analog signal to a digital signal. That is, if the signal from the tester 104 is an analog signal, the ADC 110 converts the analog signal containing the test data to a digital signal. The ADC 110 may be a 10-bit ADC, a 12-bit ADC, a 14-bit ADC, a 16-bit ADC, and/or a 20-bit ADC, and the like.

In one or more implementations, the digitally controlled oscillator (DCO) 112 is a hybrid of digital/analog electronic oscillator. The DCO 112 may be a numerically-controlled oscillator, or the like. If the signal from the tester 104 is a digital signal, the DCO 112 generates an analog signal in response that is input to the ADC 110.

In one or more implementations, the spectral analysis engine 114 aids in performing the spectral analysis of the computing device 102. Thus, spectral analysis engine 114 is a frequency transform engine that is arranged to, for example convert time-domain information to frequency information. In that light, the spectral analysis engine 114 includes the windowing module 116 and the recursive discrete Fourier transform (RDFT) module 118.

In one or more implementations, the windowing module 116 obtains test data from the tester 104 via the ADC 110, from the tester 104 via the ADC 110 and the DCO 112, or directly from the tester 104. The windowing module filters the test data to adapt the test data to the bandwidth that the RDFT module 118 utilizes. The windowing module 116 is arranged to obtain raw test data in a serial manner in real time from the computing device 102 rather than in parallel. For example, the raw test data is multiplied by the windowing coefficients of the windowing module 116 in a serial manner.

In one or more implementations, the windowing module 116 applies a Hanning window, a Hamming window, an apodizing window, or the like to the test data. In implementations in which the windowing module 116 applies a Hanning window to the test data, the windowing module 116 applies the following operation to the test data:

$$w(n) = \frac{1}{2}\left(1 - \cos\left(\frac{2\pi n}{N}\right)\right) = \frac{1}{2}\left(1 - \frac{1}{2}e^{\frac{j2\pi n}{N}} - \frac{1}{2}e^{\frac{-j2\pi n}{N}}\right) \quad (1)$$

where N is the number of samples in the test data set, and n is an index over the series $\{0 \ldots N-1\}$. In one or more implementations, the windowing module 116 is combined with the RDFT module 118 to facilitate executions of the methods discussed below.

Figure 2:
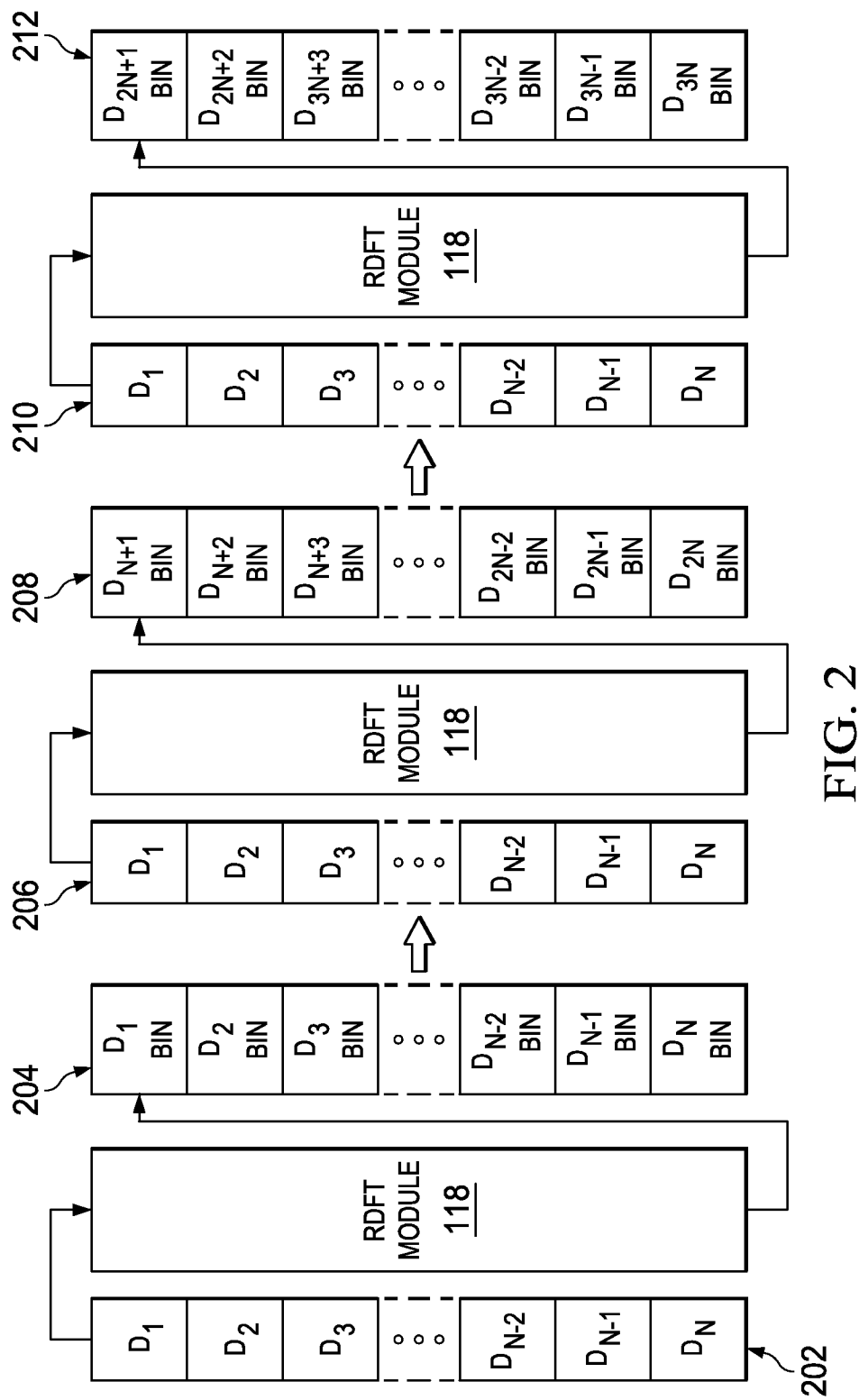
FIG. 2 is a timing diagram illustrating a discrete Fourier transform (DFT) module illustrated in FIG. 1 in accordance with exemplary embodiments of the present disclosure.

FIG. 2 is a timing diagram illustrating a recursive discrete Fourier transform (RDFT) module illustrated in FIG. 1 in accordance with exemplary embodiments of the present disclosure. In the illustrated implementation, the RDFT module 118 performs both discrete Fourier transforms (DFTs) and windowing functions. The input data includes serial data stream 202, serial data stream 204, and serial data stream 206. The results of the DFTs are sets of frequency bins 208, 210, and 212. The selection of data from the serial data streams 202, 204, and 206 are discussed below with reference to FIG. 3. The input data can include, for example, test data or functional data (e.g., data encountered in normal operation).

Each frequency bin in each set of frequency bins has a signal power. In one or more implementations, for each set of frequency bins the blind tone detection module 120 compares the signal power values from the first DFT to determine the frequency bin in the first DFT that has the greatest amplitude (which indicates the frequency bin having the greatest signal power).

For example, in one or more implementations the RDFT module 118 first performs a windowing DFT on the test data (e.g., a one hundred-point DFT) in accordance with the following equations:

$$\sum_n x(n)w(n)e^{\frac{-j2\pi kn}{N-1}} = \frac{1}{2}x(n)\left(e^{\frac{-j2\pi kn}{N-1}} - \frac{1}{2}e^{\frac{-j2\pi(k-1)n}{N-1}} - \frac{1}{2}e^{\frac{j2\pi(k+1)n}{N-1}}\right) \quad (2)$$

where k is an index over the series $\{0 \ldots N-1\}$ for the first-level DFT, and for the second- and third-level DFTs, is selected in response to an identification of the frequency bin of the previous DFT having the largest power (as described below).

By the associative property, Eq. (2) can be expressed as:

$$= \sum_n \frac{1}{2}x(n)e^{\frac{-j2\pi kn}{N-1}} - \sum_n \frac{1}{4}x(n)e^{\frac{-j2\pi(k-1)n}{N-1}} - \sum_n \frac{1}{4}x(n)e^{\frac{-j2\pi(k+1)n}{N-1}} \quad (3)$$

Assuming x(n), x'(n), and x"(n) have the same (or similar) properties, Eq. (3) can be expressed as:

$$\cong \sum_n \frac{1}{2}x(n)e^{\frac{-j2\pi kn}{N-1}} - \sum_n \frac{1}{4}x'(n)e^{\frac{-j2\pi(k-1)n}{N-1}} - \sum_n \frac{1}{4}x''(n)e^{\frac{-j2\pi(k+1)n}{N-1}} \quad (4)$$

In implementations in which the first DFT is a one hundred-point DFT, the variables in equation (2) are as follows: N=100 and k=0 to 99. The RDFT module 118 performs a first-level (recursive) DFT on the serial data stream 202 that includes $D_1$ to $D_N$ by applying the Eq. (4) to the test data. Data sets x(n), x'(n), and x"(n) are selected as described below with reference to FIG. 3. The resulting set of frequency bins is frequency bin set 204, which includes frequency bins $D_1$BIN to $D_N$BIN. For purposes of illustration assume that the blind tone detection module 120 determines that the frequency bin that has the greatest signal power is $D_{N-2}$BIN.

In one or more implementations the RDFT module 118 then performs a second-level DFT (e.g., one thousand-point DFT) in response to the first DFT frequency bin that was determined to have the greatest signal power. The increase (by a factor of 10, for example) increases the frequency resolution by decreasing the distance (the frequency quantum) between the output frequency bins. Thus, decreasing the distance between the output frequency bins effectively "zooms in" on a frequency range of interest as identified by the frequency bin generated by the first DFT as having the greatest power.

Selecting values for the variable k (in response to the identified frequency bin) allows the next DFT to zoom in on the frequency range of interest identified by the previous DFT (by increasing the frequency resolution about 10 times). Accordingly, during the second-level DFT, the RDFT module 118 applies Eq. 4 to the serial data stream 206 with $D_{N-2}$BIN (the identified frequency bin) being used to select values of k, where k ranges from a start value of (($D_{N-2}$BIN*10)−24) to an end value of (($D_{N-2}$BIN*10)+25). Thus k is selected to produce 50 new frequency bins (frequency bin set 208) that are centered about the frequency bin identified by the first-level FFT (such that the new frequency quanta spans a range defined by five of the previous frequency bins, such that at least several frequency bins of the previous DFT that are surrounded and/or are adjacent to the identified frequency bin fall within the frequency range covered by the second DFT).

The RDFT module 118 performs the second-level (recursive) DFT using the serial data stream 204 with data ranging from $D_{N+1}$ to $D_{2N}$. The resulting set of frequency bins is frequency bin set 208, which includes frequency bins $D_{N+1}$BIN to $D_{2N}$BIN that are centered about a frequency associated with the $D_{N-2}$BIN frequency bin. For purposes of explanation assume that the blind tone detection module 120 determines that the frequency bin in the second-level DFT that has the greatest signal power is $D_{2N-2}$BIN.

In one or more implementations the RDFT module 118 then performs a third-level (recursive) DFT (e.g., ten thousand-point DFT) in response to the second-level DFT frequency bin that was determined to have the greatest signal power. The increase (by a factor of 10, for example) increases the frequency resolution by decreasing the distance between the output frequency bins. Thus, decreasing the distance between the output frequency bins effectively "zooms in" on a narrower frequency range of interest as identified by the frequency bin generated by the second DFT as having the greatest power.

Selecting values for the variable k (in response to the identified frequency bin) allows the next DFT to zoom in on the frequency range of interest identified by the second-level DFT. Accordingly, during the third DFT, the RDFT module 118 applies Eq. 4 to the serial data stream 210 with $D_{2N-2}$BIN (the identified frequency bin) being used to select values of k, where k ranges from a start value of (($D_{2N-2}$BIN*10)−12) to an end value of (($D_{2N-2}$BIN*10)+13). Thus k is selected to produce 25 new frequency bins that are centered about the frequency bin identified by the second-level FFT (such that the new frequency quanta spans a range defined at least two of the previous frequency bins, such that at least several frequency bins of the previous DFT that are surrounded and/or are adjacent to the identified frequency bin fall within the frequency range covered by the second DFT).

The RDFT module 118 performs the third-level DFT using the serial data stream 208 with data ranging from $D_{2N+1}$ to $D_{3N}$. The resulting set of frequency bins is frequency bin set 212, which includes frequency bins $D_{2N+1}$BIN to $D_{3N}$BIN that are centered about a frequency associated with the $D_{2N-2}$BIN frequency bin. For purposes of explanation assume that the blind tone detection module 120 determines that the frequency bin in the third DFT that has the greatest signal power is $D_{2N-2}$BIN. For simplicity, only three levels of DFT processing are illustrated. In operation, one, two, three, four, five, six, seven, eight, nine, ten, or more levels are used.

In implementations in which the first DFT is a one hundred-point DFT, the second DFT is a one thousand-point DFT, and the third DFT is a ten thousand-point DFT, the number of calculations that the RDFT module 118 performs is 100*100+1000*50+10000*25=310,000 calculations (which is substantially less than the number of calculations performed by a conventional FFT to obtain the same quality of results). The resulting small number of calculations occurs because the values of the frequency bins are calculated sequentially (in series) and no additional cycles are used to compare the frequency bins to determine which frequency bin has the greatest signal power.

Moreover, since the (recursive) DFTs are performed using a single RDFT module 118 instead of performing 100,000,000 calculations, the recursive manner of the calculations reduces the number to 310,000 calculations. Also, each time a DFT is performed, the number of frequency bins to be calculated can be reduced, and thus the calculation time. Of course, any size and number of DFTs (or FFTs) may be used without departing from the spirit and intent of the technology described here. For example, there may be multiple DFTs, where each succeeding DFT sample size is larger than the sample size of the preceding DFT. The DFT sizes may be 200, 500, 5000, 35,000, 70,000, and the like.

The terms "frequency bin" or "frequency bins" may be used interchangeably with the terms "tone frequency" or "tone frequencies" without changing the intent or scope of the disclosure.

In one or more implementations, the spectral characteristics module 122 determines the spectral characteristics of the test data using the third DFT frequency bin that was determined to have the greatest signal power frequency. In keeping with the example, the spectral characteristics module 122 determines the spectral characteristics of the test data using bin $D_{3N-2}$BIN. For example, the spectral characteristics module 122 determines spectral characteristics such as total harmonic distortion (THD), signal-to-noise ratio (SNR), spurious-free dynamic range (SFDR), I/Q amplitude mismatch, power supply rejection ratio (PSRR), and the like.

In one or more implementations, the I/O port 124 is a Universal Serial Bus (USB), a general purpose I/O port, or the like. The I/O port 124 is used to transfer the results of the spectral characteristics out from the computing device 102.

In one or more implementations, the CPU 126 is a Complex Instruction Set Computer (CISC)-type CPU, a Reduced Instruction Set Computer (RISC)-type CPU, a digital signal processor (DSP), or the like. The CPU 126 also can be a programmable digital module or any device that is used to process signals or data.

Figure 3:
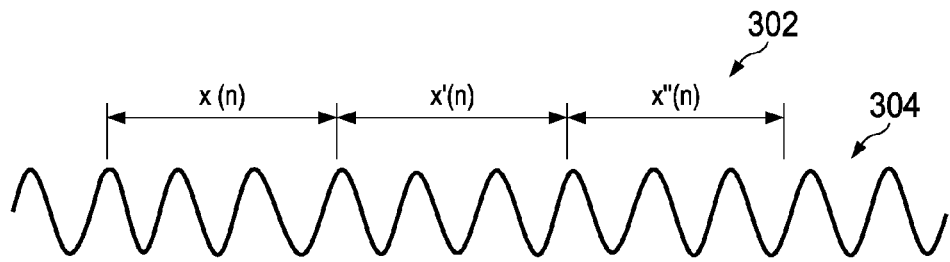
FIG. 3 is a timing diagram illustrating sample set generation for a DFT module in accordance with exemplary embodiments of the present disclosure.

FIG. 3 illustrates example test data according to one or more implementations described herein. The illustrated test data includes data set 302 and data stream 304. The illustrated test data 302 is obtained from the data stream 304 at any convenient region of the data stream in the data stream 304. For example, the x(n) data is used for a first summation term of the DFT, the x'(n) data is used for a second summation term of the DFT, and the x' (n) data is used for a third summation term of the DFT. The data can be obtained from a data stream on an as-needed basis because the frequency information in the data stream 304 is time invariant and the frequency content does not vary. Thus, separate regions of the data stream are used for each summation term of Eq. 4. In addition, a substantial amount of storage space required to perform (portions of) the DFT is eliminated.

Figure 4:
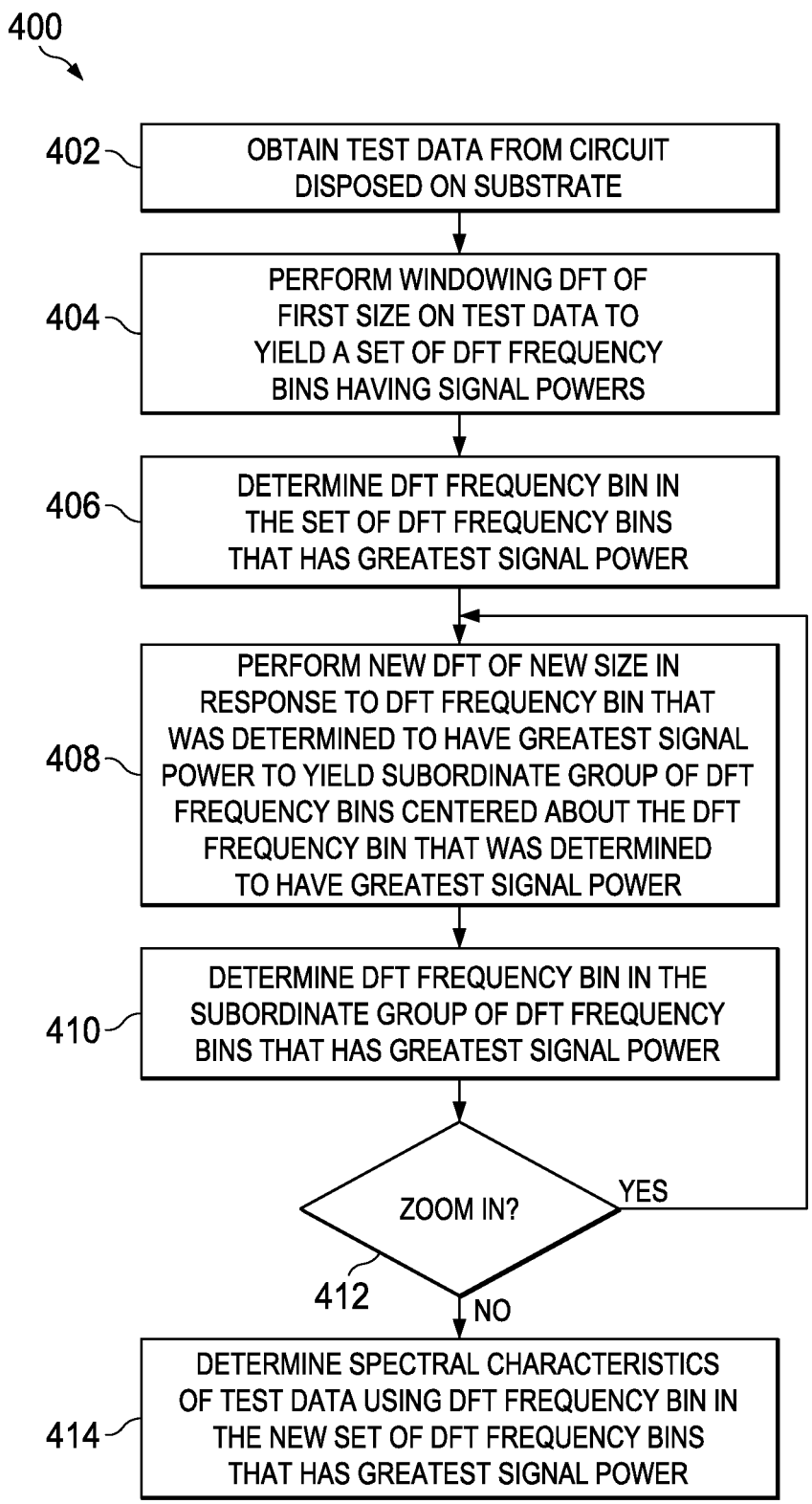
FIG. 4 illustrates a flow diagram for determining spectral characteristics of circuits in accordance with one or more exemplary embodiments of the present disclosure.

FIG. 4 is a flowchart of a method 400 for determining spectral characteristics of circuits implemented by the computing device 102 using a recursive discrete Fourier transform (RDFT) according to the technology described herein. Program flow is initiated in block 402.

In a block 402, the method 400 obtains test data from a circuit disposed on a substrate. In one or more implementations, the signal processor 108 obtains test data 202 from the tester 104 via the spectrum analyzer 106.

In a block 404, the method 400 performs a windowing DFT of a first size on the test data to yield a set of DFT frequency bins. The first FFT yields a set of frequency bins. Each frequency bin has a signal power. In one or more implementations, the windowing module 116 windows the obtained test data using a Hanning window, a Hamming window, or an apodization window, for example, and the RDFT module 118 performs a one hundred-point FFT on the windowed test data 202, which includes $D_1$ to $D_N$. The first FFT yields the set 208 of frequency bins $D_1BIN$ to $D_NBIN$.

In a block 406, the method 400 determines the frequency bin in the set of frequency bins from the first DFT that has the greatest amplitude and/or signal power. In one or more implementations, the blind tone detection module 120 determines the frequency bin in the set of frequency bins that has the greatest signal power. For example, the blind tone detection module 120 determines that the frequency bin in the set 208 of frequency bins $D_1BIN$ to $D_NBIN$ that has the greatest signal power is $D_{N-2}BIN$.

In a block 408, the method 400 performs a new FFT of a new size on the test data. The new FFT yields a subordinate group of frequency bins for the frequency bin that was determined to have the greatest signal power in the first FFT. Each frequency bin in the new FFT has a signal power. In one or more implementations, the RDFT module 118 performs a thousand-point FFT on the frequency bin $D_{N-2}BIN$. The resulting subordinate group of frequency bins is frequency bin set 210, which includes frequency bins $D_{N+1}BIN$ to $D_{2N}BIN$.

In a block 410, the method 400 determines the frequency bin in the subordinate group of frequency bins that has the greatest signal power. In one or more implementations, the blind tone detection module 120 determines the frequency bin in the subordinate group of frequency bins that has the greatest signal power. For example, the blind tone detection module 120 determines that the frequency bin 210 that has the greatest signal power is $D_{2N-2}BIN$.

In a block 412, the method 400 determines whether to zoom in to the vicinity of the frequency bin in the subordinate group of frequency bins that was determined to have the greatest signal power in block 410. If the method 400 makes the determination to zoom in to the vicinity of the frequency bin in the subordinate group of frequency bins that was determined to have the greatest signal power in block 410, then control of the method 400 passes to block 408, and the method 400 performs a new FFT of a new size on frequency bin in the subordinate group of frequency bins that has the greatest signal power (i.e., $D_{2N-2}BIN$).

If on the other hand the method 400 makes the determination not to zoom in to the vicinity of the frequency bin in the subordinate group of frequency bins that was determined to have the greatest signal power in block 410, then control of the method 400 passes to a block 414. In block 414, the method 400 uses the subordinate group of frequency bins that was determined to have the greatest signal power in block 410 to determine the spectral characteristics of the test data. In one or more implementations, the spectral characteristics module 122 determines spectral characteristics, such as THD, SNR, and the like, of the test data.

The method 400 is illustrated as a collection of actions in a logical flow graph, which represents a sequence of operations that can be implemented in mechanics alone or a combination with hardware, software, and/or firmware. In the context of software/firmware, the actions represent instructions stored on one or more computer-readable storage media that, when executed by one or more processors, perform the recited operations. Note that the order in which the processes are described is not intended to be construed as a limitation, and any number of the described process blocks can be combined in any order to implement the processes or an alternate process. For example, an alternate frequency bin can be examined to determine a level of noise to be compared with a signal frequency bin (e.g., the frequency bin having the greatest level of power at a desired resolution) to calculate a signal-to-noise (SNR) ratio. As another example, the frequency bins having the second and third greatest powers can be determined and used (with the power level of the bin having the highest power level, for example) to determine a total harmonic distortion (THD) metric. Additionally, individual actions may be deleted from the processes without departing from the spirit and scope of the subject matter described herein.

Figure 5:
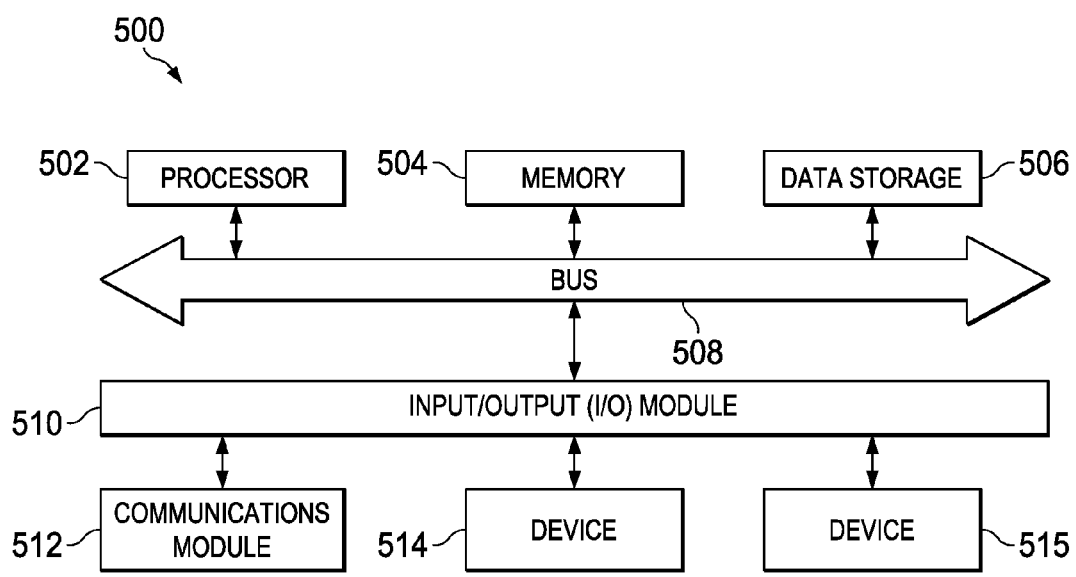
FIG. 5 is a high-level block diagram illustrating an example computer system device in accordance with exemplary embodiments of the disclosure.

FIG. 5 is a high-level block diagram illustrating an example computer system 500 suitable for implementing the computing device 102 of FIG. 1. In certain aspects, the computer system 500 may be implemented using hardware or a combination of software and hardware.

The illustrated computer system 500 includes a processor 502, a memory 504, and data storage 506 coupled to a bus 508 or other communication mechanism for communicating information. An input/output (I/O) module 510 is also coupled to the bus 508. A communications module 512, a device 514, and a device 516 are coupled to the I/O module 510.

The processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. The processor 502 may be used for processing information. The processor 502 can be supplemented by, or incorporated in, special purpose logic circuitry.

The memory 504 may be Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device used for storing information, a computer program, and/or instructions to be executed by the processor 502. The memory 504 may store code that creates an execution environment for one or more computer programs used to implement technology described herein.

A computer program as discussed herein does not necessarily correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one processor, multiple processors, one computer or on multiple computers that are located at one site or distributed across multiple sites and interconnected by a communication network.

Unless indicated otherwise by the context, a module refers to a component that is hardware, firmware, and/or a combination thereof with software (e.g., a computer program.) A computer program as discussed herein does not necessarily correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The instructions may be implemented in one or more computer program products, e.g., one or more modules of computer program instructions encoded on one or more computer readable media for execution by, or to control the operation of, the computer system 500, and according to any method well known to those of skill in the art. The term "computer-readable media" includes computer-storage media. For example, computer-storage media may include, but are not limited to, magnetic storage devices (e.g., hard disk, floppy disk, and magnetic strips), optical disks (e.g., compact disks (CD) and digital versatile disks (DVD)), smart cards, flash memory devices (e.g., thumb drives, "sticks", key drive, and SD cards), and volatile and non-volatile memory (e.g., random access memory (RAM), read-only memory (ROM)).

The data storage 506 may be a magnetic disk or optical disk, for example. The data storage 506 may function to store information and instructions to be used by the processor 502 and other components in the computer system 500.

The bus 508 may be any suitable mechanism that allows information to be exchanged between components coupled to the bus 508. For example, the bus 508 may be transmission media such as coaxial cables, copper wire, and fiber optics, optical signals, and the like.

The I/O module 510 can be any input/output module. Example input/output modules 510 include data ports such as Universal Serial Bus (USB) ports.

The communications module 512 may include networking interface cards, such as Ethernet cards and modems.

The device 514 may be an input device. Example devices 514 include a keyboard, a pointing device, a mouse, or a trackball, by which a user can provide input to the computer system 500.

The device 516 may be an output device. Example devices 516 include displays such as cathode ray tubes (CRT) or liquid crystal display (LCD) monitors that display information, such as web pages, for example, to the user.

One or more implementations are described herein with reference to illustrations for particular applications. It should be understood that the implementations are not intended to be limiting. Those skilled in the art with access to the teachings provided herein will recognize additional modifications, applications, and implementations within the scope thereof and additional fields in which the technology would be of significant utility. In the above description of example implementations, for purposes of explanation, specific numbers, materials, configurations, and other details are set forth in order to better explain implementations as claimed. However, it will be apparent to one skilled in the art that the claims may be practiced using details different than the examples described herein. In other instances, well-known features are omitted or simplified to clarify the description of the example implementations.

For example, it will be appreciated that several of the above-disclosed and other features and functions, or alternatives thereof, may be combined into many other different systems or applications. Also, it will be appreciated that various presently unforeseen or unanticipated alternatives, modifications, variations or improvements therein may be subsequently made by those skilled in the art, which are also intended to be encompassed by the claims that follow.

In the claims appended herein, the inventor invokes 35 U.S.C. §112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. §112, paragraph 6. The various embodiments described above are provided by way of illustration only and should not be construed to limit the claims attached hereto. Those skilled in the art will readily recognize various modifications and changes that could be made without following the example embodiments and applications illustrated and described herein, and without departing from the true spirit and scope of the following claims.

What is claimed is:

1. A signal processor disposed on a substrate comprising:
a frequency transform module that is configured to obtain time-domain test data from a circuit disposed on the substrate and to perform a first frequency transform on a first sample set of the time-domain test data to generate a first-level set of frequency bins spanning a first frequency range; and
a frequency-bin power module that is configured to determine a first-level frequency bin within the first-level set of frequency bins that has a greatest signal power,
wherein the frequency transform module is configured to perform a second frequency transform on a second sample set of the time-domain test data to generate a second-level set of frequency bins spanning a second frequency range that is selected in response to the determined greatest signal power first-level frequency bin, wherein each frequency bin in the second-level set of frequency bins is separated from adjacent frequency bins in the second-level set of frequency bins by a second frequency spacing that is less than a first frequency spacing of adjacent bins in the first-level set of frequency bins, and wherein the frequency-bin power module is configured to determine a second-level frequency bin within the second-level set of frequency bins that has a greatest signal power;

wherein the second-level frequency bin within the second-level set of frequency bins that has a greatest signal power is used to increase the speed at which the signal processor operates.

2. The signal processor according to claim 1 wherein the first-level set of frequency bins is smaller than the second-level set of frequency bins.

3. The signal processor according to claim 2 wherein the second frequency range is smaller than the first frequency range.

4. The signal processor according to claim 1 wherein the second frequency range includes the frequency range of a consecutive plurality of first-level frequency bins that includes the determined greatest signal power first-level frequency bin.

5. The signal processor according to claim 1 wherein the time-domain test data is obtained from a data stream having fixed frequency content.

6. The signal processor according to claim 1 wherein the first sample set of the time-domain test data and the second sample set of the time-domain test data are obtained from separate regions of the data stream.

7. The signal processor according to claim 1 wherein the first frequency transform and the second frequency transform are performed in accordance with the formula:

$$\sum_n \frac{1}{2} x(n) e^{\frac{-j2\pi k n}{N-1}} - \sum_n \frac{1}{4} x'(n) e^{\frac{-j2\pi(k-1)n}{N-1}} - \sum_n \frac{1}{4} x''(n) e^{\frac{-j2\pi(k+1)n}{N-1}}$$

wherein N is the number of samples in the test data set, n is an index over the series $\{0 \ldots N-1\}$, k is an index over the series $\{0 \ldots N-1\}$ for the first frequency transform and is selected for the second frequency transform in response to the determined greatest signal power first-level frequency bin, and x(n), x'(n), and x''(n) are data sets selected from separate regions of the data stream.

8. The signal processor according to claim 1 wherein the frequency transform module is configured to perform a third frequency transform on a third sample set of the time-domain test data to generate a third-level set of frequency bins spanning a third frequency range that is selected in response to the determined greatest signal power second-level frequency bin, wherein each frequency bin in the third-level set of frequency bins is separated from adjacent frequency bins in the third-level set of frequency bins by a third frequency spacing that is less than a second frequency spacing of adjacent bins in the second-level set of frequency bins, and wherein the frequency-bin power module is configured to determine a third-level frequency bin within the third-level set of frequency bins that has a greatest signal power.

9. The signal processor according to claim 1 comprising a windowing module that includes at least one of an apodization window, a Hanning window, and a Hamming window and wherein the windowing module is configured to apply windowing coefficients to the obtained test data in real time.

10. The signal processor according to claim 9 wherein the signal processor disposed on the substrate is arranged to obtain the test data and to convert the analog test data into a digital signal.

11. The signal processor according to claim 1 comprising a spectral-characteristics module that is configured to use the determined greatest signal power second-level frequency bin to determine the spectral characteristics of the test data.

12. A method performed on a substrate comprising:
obtaining time-domain test data from a circuit disposed on the substrate, wherein the time-domain test data is arranged having frequency content;
windowing the obtained test data;
performing a first frequency transform on a first sample set of the time-domain test data to generate a first-level set of frequency bins spanning a first frequency range;
determining a first-level frequency bin within the first-level set of frequency bins that has a greatest signal power;
performing a second frequency transform on a second sample set of the time-domain test data to generate a second-level set of frequency bins spanning a second frequency range that is selected in response to the determined greatest signal power first-level frequency bin, wherein each frequency bin in the second-level set of frequency bins is separated from adjacent frequency bins in the second-level set of frequency bins by a second frequency spacing that is less than a first frequency spacing of adjacent bins in the first-level set of frequency bins; and
determining a second-level frequency bin within the second-level set of frequency bins that has a greatest signal power;
wherein the second-level frequency bin within the second-level set of frequency bins that has a greatest signal power is used to increase the speed at which the signal processor operates.

13. The method according to claim 12 comprising using the determined greatest signal power first-level frequency bin to determine the spectral characteristics of the test signal.

14. The method according to claim 13 comprising using a circuit disposed on the substrate to determine whether the circuit disposed on the substrate is functionally correct by comparing the determined spectral characteristics of the test signal with the frequency content of the time-domain test data.

15. The method according to claim 12 wherein the first-level set of frequency bins is smaller than the second-level set of frequency bins and wherein the second frequency range is smaller than the first frequency range.

16. The method according to claim 12 comprising:
performing a third frequency transform on a third sample set of the time-domain test data to generate a third-level set of frequency bins spanning a third frequency range that is selected in response to the determined greatest signal power second-level frequency bin, wherein each frequency bin in the third-level set of frequency bins is separated from adjacent frequency bins in the third-level set of frequency bins by a third frequency spacing that is less than a second frequency spacing of adjacent bins in the second-level set of frequency bins; and
determining a third-level frequency bin within the second-level set of frequency bins that has a greatest signal power.

17. A mixed-signal processing system disposed on a substrate comprising:
- a processor on the substrate that is arranged to generate time-domain test data having a defined frequency content;
- a frequency transform module that is configured to perform a first frequency transform on a first sample set of the time-domain test data to generate a first-level set of frequency bins spanning a first frequency range; and
- a frequency-bin power module that is configured to determine a first-level frequency bin within the first-level set of frequency bins that has a greatest signal power,
- wherein the frequency transform module is configured to perform a second frequency transform on a second sample set of the time-domain test data to generate a second-level set of frequency bins spanning a second frequency range that is selected in response to the determined greatest signal power first-level frequency bin, wherein each frequency bin in the second-level set of frequency bins is separated from adjacent frequency bins in the second-level set of frequency bins by a second frequency spacing that is less than a first frequency spacing of adjacent bins in the first-level set of frequency bins, and
- wherein the frequency-bin power module is configured to determine a second-level frequency bin within the second-level set of frequency bins that has a greatest signal power;
- wherein the second-level frequency bin within the second-level set of frequency bins that has a greatest signal power is used to increase the speed at which the signal processor operates.

18. The system according to claim 17 wherein the frequency transform module is configured to perform a third frequency transform on a third sample set of the time-domain test data to generate a third-level set of frequency bins spanning a third frequency range that is selected in response to the determined greatest signal power second-level frequency bin, wherein each frequency bin in the third-level set of frequency bins is separated from adjacent frequency bins in the third-level set of frequency bins by a third frequency spacing that is less than a second frequency spacing of adjacent bins in the second-level set of frequency bins, and wherein the frequency-bin power module is configured to determine a third-level frequency bin within the third-level set of frequency bins that has a greatest signal power.

19. The system according to claim 17 wherein the first-level set of frequency bins is smaller than the second-level set of frequency bins and wherein the second frequency range is smaller than the first frequency range.

20. The system according to claim 19 wherein the processor disposed on the substrate is arranged to determine whether the circuit disposed on the substrate is functionally correct by comparing the determined spectral characteristics of the test signal with the frequency content of the time-domain test data.

* * * * *